(12) United States Patent
Kuentz et al.

(10) Patent No.: US 7,642,903 B2
(45) Date of Patent: Jan. 5, 2010

(54) TRAILER TIRE ALERT SYSTEM

(76) Inventors: Charles L. Kuentz, 403 Oak Country St., Helotes, TX (US) 78023; Judith Kuentz, 403 Oak Country St., Helotes, TX (US) 78023

( * ) Notice: Subject to any disclaimer, the term of this patent is extended or adjusted under 35 U.S.C. 154(b) by 257 days.

(21) Appl. No.: 11/501,623

(22) Filed: Aug. 8, 2006

(65) Prior Publication Data

US 2008/0042818 A1 Feb. 21, 2008

Related U.S. Application Data

(63) Continuation of application No. 10/487,116, filed as application No. PCT/EP02/09365 on Aug. 21, 2002, now abandoned.

(30) Foreign Application Priority Data

Aug. 22, 2001 (GB) ................................ 0120441.1

(51) Int. Cl.
*B60C 23/00* (2006.01)
(52) U.S. Cl. ....................... 340/442; 340/443; 340/444; 340/445

(58) Field of Classification Search ................. 340/442, 340/443, 444, 445
See application file for complete search history.

(56) References Cited

U.S. PATENT DOCUMENTS 4,173,011 A * 10/1979 Gibson ........................ 340/443
6,466,127 B1 * 10/2002 Martin ........................ 340/443

* cited by examiner

*Primary Examiner*—Benjamin C Lee
*Assistant Examiner*—Ojiako Nwugo
(74) *Attorney, Agent, or Firm*—Raymond M. Galasso; Galasso & Associates, L.P.

(57) ABSTRACT

A tire pressure sensing device for a tow trailer that signals the driver of the tow vehicle subsequent to deflation of at least one tire mounted to the trailer. The tire pressure sensing device further includes a base plate mounted to the axle of the tow trailer releasably secured by a generally u-shaped clamp. A switch is superposed on the base plate. The switch further includes an actuating rod support member and an actuating rod extending in a downward direction. The actuating rod biases the switch to a closed position subsequent to deflation of the tire thereby electrically activating a warning indicator.

17 Claims, 2 Drawing Sheets

Fig. II

TRAILER TIRE ALERT SYSTEM

This application is a Continuation of U.S. application Ser. No. 10/487,116 filed Apr. 6, 2004 now abandoned, which is a US National 371 phase filing of International Application PCT/EP 02/09365 filed Aug. 21, 2002 which claims priority to Application No. 0120441.1 filed in Great Britain on Aug. 22, 2001.

FIELD OF THE INVENTION

The present invention relates a tire pressure indication device, more specifically a trailer tire pressure indicator and alert system that is releasably secured to the axle of a trailer that has a portion which engages with the ground upon the deflation of the adjacent tire.

BACKGROUND

Thousands of drivers tow trailers behind their vehicles every day. From recreational trailers to commercial tractor trailers, towing these trailers can present numerous difficulties for the drivers. Stopping distance is lengthened and handling is cumbersome when a trailer has a heavy load disposed thereon.

One particular challenge with multi-axle trailers is detecting when the tire pressure of the trailer tire has become low so as to present a potential hazard. The rear axle trailer tires are extremely difficult to see even with the proper towing mirrors on the tow vehicle. Vision of these tires is usually blocked by the fender well and the tire adjacently in front. Additionally, these trailers have a plurality of tires which makes it almost impossible for a driver to notice a handling difference when only one tire has become partially deflated. A partially deflated tire rises to a higher temperature than a tire with correct air pressure. This higher temperature increases the risk for a blowout. Low tire pressure can also increase the difficulty in handling the trailer. As these trailers are heavy and can long, this present a significant potential for an accident resulting in damage to the trailer and its contents. Furthermore, trailers in this condition present a safety hazard to other motorists nearby.

Accordingly, there is a need for a trailer tire pressure sensing device that can signal to the driver in the tow vehicle when a tire has become partially deflated.

SUMMARY OF THE INVENTION

It is the object of the present invention is to provide a device that is mounted on at least one axle on a trailer that will, upon deflation of at least one proximate tire on the trailer, provide a signal to the driver indicating such deflation.

It is a further object of the present invention to provide a device that is normally not engaged with the ground when the tires on the trailer are mounted and inflated properly.

Another object of the present invention is to provide a tire deflation sensing device for a trailer being towed by a vehicle that has an electrical circuit that is normally open when the tires are properly inflated and wherein the circuit will be closed when a portion of the tire deflation sensing device contacts the ground.

Yet another object of the present invention is to provide a tire deflation sensing device for a trailer being towed by a vehicle that uses a resilient rod and tube to contact the ground thereby activating a switch and completing the electrical circuit.

To the accomplishment of the above and related objects the present invention may be embodied in the form illustrated in the accompanying drawings. Attention is called to the fact that the drawing are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
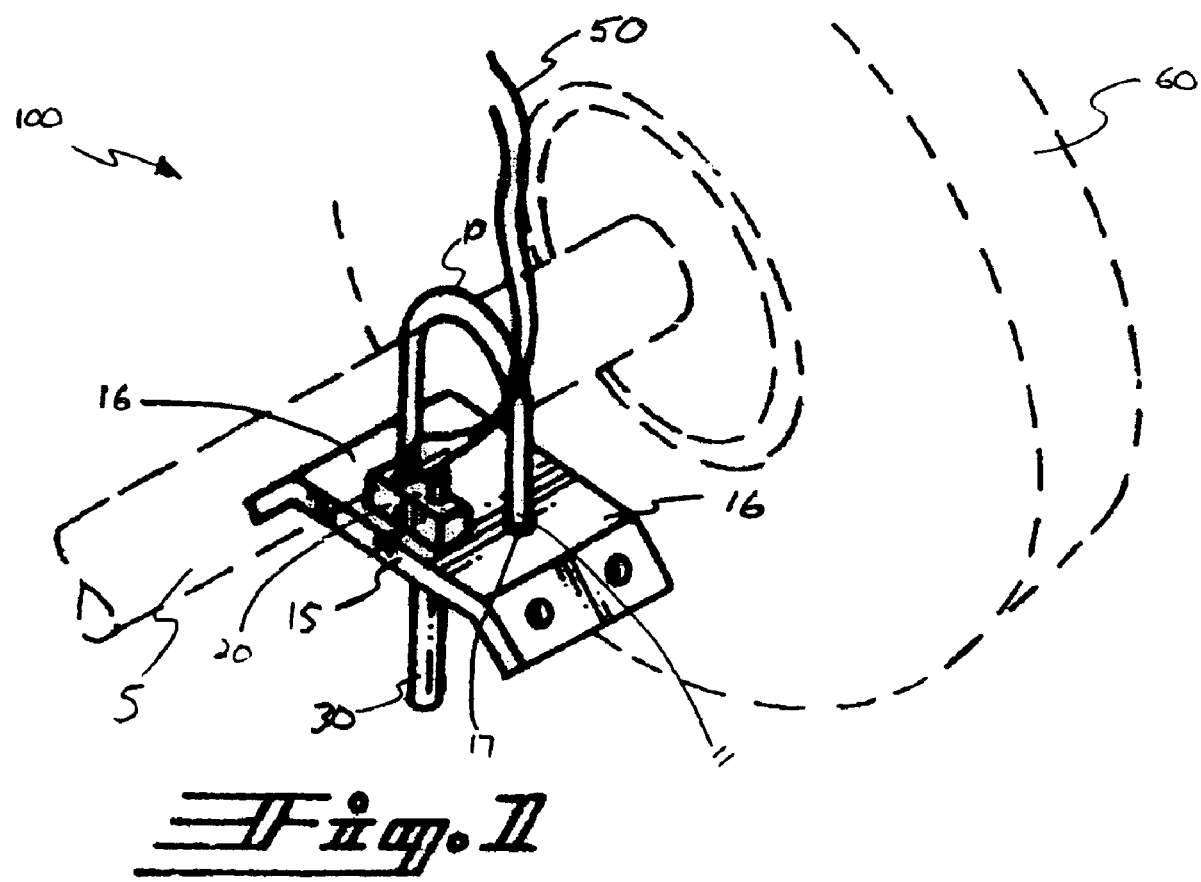
FIG. 1 is a perspective view of an embodiment of the present invention mounted to an axle of a trailer with the axle and wheel of the trailer illustrated in dashed lines.
Figure 2:
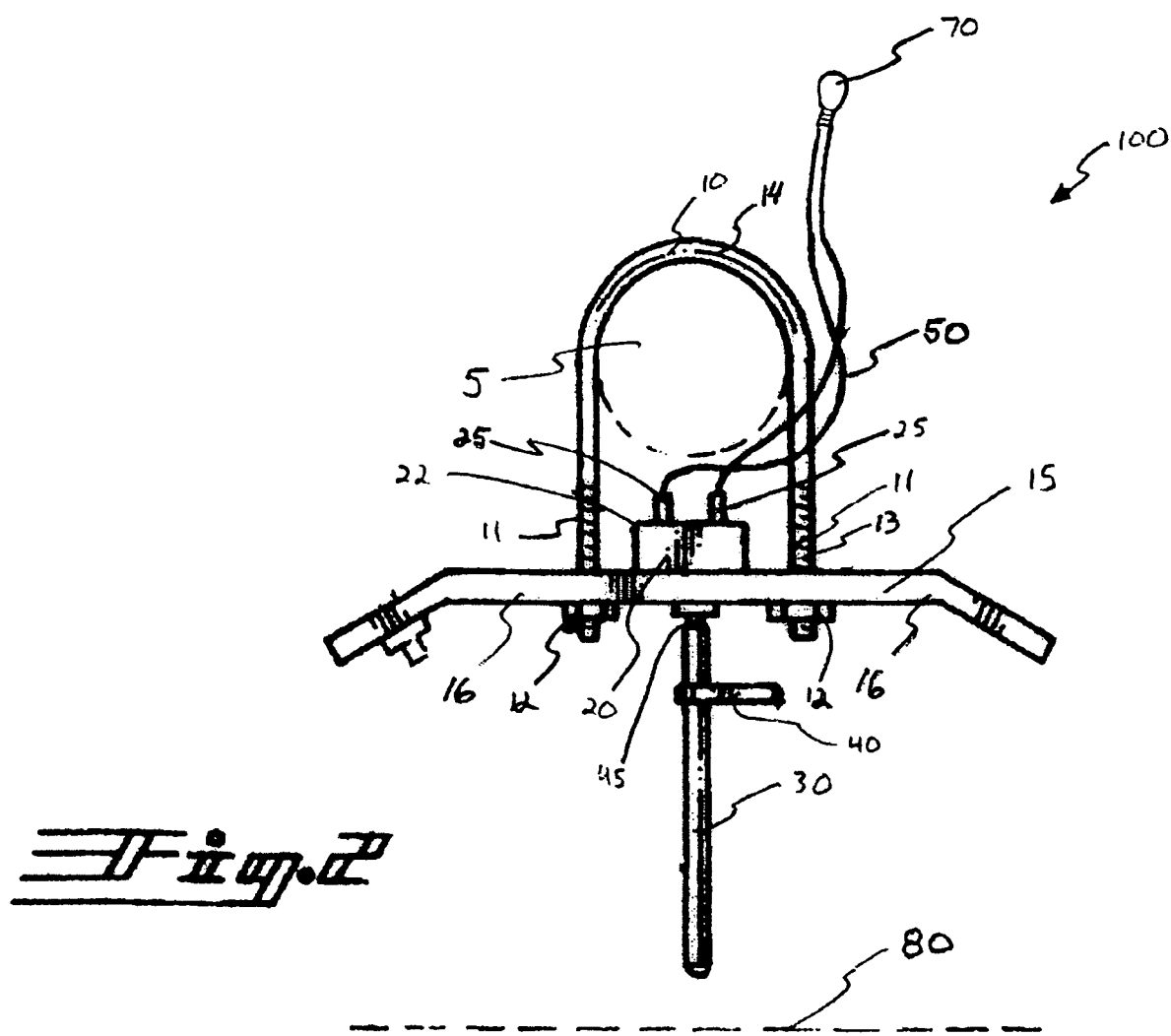
FIG. 2 is a side view of an embodiment of the present invention.

Now referring in particular to the drawings submitted herewith, wherein the various elements are not necessarily drawn to scale and wherein like reference numerals are used for like elements through the figures, there is illustrated a tire deflation signal device 100 constructed according to the principles of the present invention.

The tire deflation signal device 100 comprises a mounting clamp 10 to releasably secure the tire deflation signal device 100 to an axle 5 of a conventional trailer. Those skilled in the art should recognize that the tire deflation signal device 100 could be mounted to numerous different types of trailers. More specifically but not by way of limitation, the tire deflation signal device 100 could be mounted to a boat trailer or travel trailer.

The mounting clamp 10 is secured to the axle 5 proximate to and inside the tire 60 in at least one position on a conventional trailer. It is further contemplated within the scope of the present invention that a tire deflation signal device 100 could be mounted proximate to each tire on a trailer. The mounting clamp 10 is generally a unshaped bolt having two ends 11 that extend downward from the axle 5. Each end 11 of the mounting clamp 10 has conventional threads 13 circumferentially disposed on a portion thereof. Interposed the two ends 11 of the mounting clamp 10 and contiguous therewith is a generally arcuate section 14. The arcuate section 14 is of sufficient radius to correspond with the radius of the trailer axle upon which it is to be mounted.

The mounting clamp 10 is manufactured from a suitable durable material such as but not limited to zinc or steel. Those skilled in the art should recognize that numerous different types of mounting clamps 10 could be utilized to conform or mate with the shape of the axle 5 of the trailer in order to provide a stable connection.

Secured to each end 11 of the mounting clamp 10 is a base plate 15. The base plate 15 is positioned generally adjacent to and underneath the axle 5. The base plate 15 is configured to be attached in a substantially horizontal manner with a portion 16 extending laterally from both sides of the axle 5. The base plate 15 is manufactured from a suitable durable material such as but not limited to galvanized steel. Each end 11 of the mounting clamp 10 extends through a corresponding aperture 17 in the base plate 15 and is releasably secured with a fastener 12. Those skilled in the art will recognize that numerous different types of fasteners 12 could be utilized to secured the mounting clamp 10 to the base plate 15. More specifically but not by way of limitation, the fasteners 12 could be conventional nylon insert nuts or wing nuts.

Superposed on the base plate 15 is a switch housing 22. The switch housing 22 is generally rectangular in shape and substantially hollow. The switch housing 22 is manufactured from a suitable durable material such as thermoplastics. The switch housing 22 is water resistant to protect the switch 20 disposed inside. The switch 20 is contained within the switch housing 22 and is manufactured from a conventional self-centering normally open switch. The switch 20 and switch housing 22 are secured to the base plate 15 by conventional mechanical or chemical methods. The switch 20 has an actuating rod support member 45 extending downward through the base plate 15. The actuating rod support member 45 is positioned generally perpendicular to the base plate 15. The actuating rod support member 45 is manufactured from a suitable durable material such as steel. The actuating rod support member 45 is sealably connected to the switch 20 to inhibit water from propagating into the switch housing 22.

The actuating rod support member 45 is pivotally mounted to the switch 20. The actuating rod support member 45 can pivot in either a generally forwards and backwards direction. Surroundably mounted to one end of the actuating rod support member 45 opposite the switch 20 is an actuating rod 30. The actuating rod 30 is surroundably mounted to the actuating rod support member 45 and is generally contiguous therewith. The actuating rod 30 extends downward to a predetermined point so as to be disengaged with the ground 80 when the adjacent tire 60 is properly inflated.

The actuating rod 30 is manufactured from a semi-flexible plastic tube. The actuating rod 30 is secured to the actuating rod support member 45 using a strap 40. Although no particular type of strap 40 is required, good results have been achieved with a strap 40 that is a nylon tie strap. Those skilled in the art should recognize that numerous different type of straps could be used in place of and/or in conjunction with the strap 40 as described herein.

Utilizing a semi-flexible material provides flexible compensation for the vertical component of the force present on the actuating rod 30 subsequent to deflation of the tire 60. The switch 20 is in an open condition when the actuating rod 30 is extending downward and generally perpendicular to the base plate 15. Subsequent to a tire deflation, the actuating rod 30 contacts the ground 80 underneath thereby causing the actuating rod support member 45 to pivot in either a backwards or forwards direction depending on the travel direction of the trailer. Ensuing to pivoting due to contact with the ground 80, the switch 20 is moved to its closed position whereby a circuit is completed which results in a current traveling through the circuit thereby activating the warning light 70 that has been installed where it can be easily observed by the driver of the tow vehicle. Those skilled in the art will recognize that numerous different styles of lights could be utilized as a warning light 70. More specifically but not by way of limitation, the warning light 70 could be manufactured from a conventional LED light. It is further contemplated within the scope of the present invention that the warning light 70 could be mounted in a plurality of visible positions. More specifically but not by way of limitation, the warning light could be mounted in the passenger compartment of the tow vehicle or at a position on the trailer that can be easily seen in a tow vehicles rear view mirror.

The switch 20 is in loop with a conventional electrical circuit that is powered by a standard 12 volt car battery. It is further contemplated that the circuit has in line a 20-amp fuse with the circuit further consisting of 14-gauge wire. The wire 50 is conventional insulated wire 50 that can be secured to the trailer frame and extended to connect with the tow vehicle using conventional trailer connections. Although no specific amount of wire 50 is required, good results have been achieved utilizing approximately fifty foot of wire 50. The wire 50 is connected to the switch leads 25 that are superposed the switch housing 22. The switch leads 25 are conventional copper leads that are designated with opposite polarities of positive and negative. It is further contemplated in the scope of the present invention that there could be more than one tire deflation sensing device 100 mounted on the trailer as a part of a single electrical circuit with the tire deflation sensing device 100 being in a series on the electrical circuit. More specifically but not by way of limitation, a conventional tandem axle trailer could have mounted thereon four tire deflation sensing devices 100. Those skilled in the art should recognize that by utilizing a semi-flexible actuating rod 30, the tire deflation signal device 100 could be activated when the trailer is stationary. Utilizing the semi-flexible actuating rod 30 allows the actuating rod 30 to bend when engaged with the ground when the trailer is in a stationary condition. This facilitates the pivoting of the actuating rod support member 45 thereby closing the electrical circuit and activating the warning light 70.

A detailed description of the operation of a preferred embodiment of tire deflation sensing device 100 is as follows. In use, at least one tire deflation sensing device 100 is mounted to an axle 5 of a conventional trailer proximate to a tire 60 that has been inflated to the proper tire pressure. The actuating rod 30 is positioned such that it will be disengaged with the ground when the adjacent tire is in this condition. The warning light 70 is mounted in a desired position and the wires 50 are used to connect the warning light 70 to the switch 20 to form a circuit with the switch 20 being intermediate the circuit and in an open position. The tire deflation signal device 100 is further connected to the 12 volt battery of the tow vehicle. The user can then tow the trailer to its desired location while monitoring the warning light 70. If a tire 60 on the trailer begins to deflate, either while in motion or stationary, the actuating rod 30 will become engaged with the ground.

Subsequent to becoming engaged with the ground, the switch 20 is moved to its closed position, thereby completing the electrical circuit of the tire deflation sensing device 100. Ensuing circuit completion, the warning light 70 will be activated to alert the driver that the trailer tire 60 is below acceptable tire pressure. The driver then remedies the tire pressure issue which will then return the actuating rod 30 to its first position whereby it is generally perpendicular to the base plate and disengaged with the ground 80. In this position, the switch 20 returns to its normally open state and the warning light 70 is deactivated. The driver resumes normal use of the trailer.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A device for detecting low tire pressure for a tow trailer, comprising:
   a switch supported on a base plate and positioned proximate at least one tire of the tow trailer, said switch switchable between an open position and a closed position, said switch being a normally open switch; said base plate configured to be mounted adjacent to an axle of the tow trailer;
   a mounting clamp mounted around the axle to support the base plate; said mounting clamp having two ends; said two ends releasably secured to said base plate;
   an actuating rod support member mounted to the base plate and pivotally connected to said switch, for supporting an actuating rod that is operable to switch said switch between said open position and said closed position;
   said actuating rod surroundably mounted to one end of the actuating rod support member and tightened by a strap on a side of the base plate opposite the switch; said actuating rod extending downward to a predetermined point proximate the ground surface under the tow trailer; and
   a warning device connected to said switch and operable when said switch is in said closed position;
   wherein when said actuating rod engages the surface under the tow trailer when the tire pressure of the tow trailer drops to a determined level said actuating rod switches said switch to said closed position.

2. The device as recited in claim 1, and further including a mount, said mount configured to securely receive said switch.

3. The device as recited in claim 1, wherein said warming device includes a light.

4. The device as recited in claim 3, and further including a DC power source connected to said switch for supplying power to said warming device.

5. The device as recited in claim 4, wherein said warning device is substantially disposed within a vehicle connectable to the tow trailer.

6. A pressure monitoring and warning device for monitoring the pressure of at least one tire of a tow trailer, said pressure monitoring and warning device comprising:
   a switch supported on a base plate and mounted proximate the tire of the tow trailer, said switch switchable between on open position and a closed position, said switch being a normally open switch;
   an actuating rod support member mounted to the base plate and pivotally connected to said switch, said actuating rod operable to switch said switch between said open position and said closed position;
   a warning device connected to said switch and operable when said switch is in said closed position;
   an actuating rod surroundably mounted to one end of the actuating rod support member and tightened by a strap on a side of the base plate opposite the switch; said actuating rod extending downward to a predetermined point proximate the ground surface under the tow trailer; and
   wherein when said actuating rod engages the surface under the tow trailer when the tire pressure of the tow trailer drops to a determined level said actuating rod pivots thereby switching said switch to said closed position.

7. The pressure monitoring and warning device as recited in claim 6, and further including a mount, said mount configured to securely receive said switch.

8. The pressure monitoring and warning device as recited in claim 7, wherein said mount includes a base plate, said base plate configured to be mounted adjacent to an axle of the tow trailer.

9. The pressure monitoring and warning device as recited in claim 8, and further including a clamp, said clamp configured to releasably secure said base plate to said axle.

10. The pressure monitoring and warning device as recited in claim 6, wherein said warning device includes a light.

11. The pressure monitoring and warning device as recited in claim 10, and further including a DC power source connected to said switch for supplying power to said warning device.

12. A pressure monitoring and warning device for monitoring the pressure of at least one tire of a tow trailer, said pressure monitoring and warning device comprising:
   a switch supported on a base plate and mounted proximate the tire of the tow trailer, said switch switchable between an open position and a closed position, said switch being normally open switch;
   a mount configured to releasably receive said switch;
   an actuating rod support member mounted to the base plate and connected to said switch, said actuating rod operable to switch said switch between said open position and said closed position;
   an actuating rod surroundably mounted and generally contiguous with one end of the actuating rod support member by a strap opposite the switch; said actuating rod extending downward to a predetermined point proximate the ground surface under the tow trailer;
   a warning device connected to said switch and operable when said switch is in said closed position;
   wherein when said actuating rod engages the surface under the tow trailer when the tire pressure of the tow trailer drops to a determined level said actuating rod switches said switch to said closed position.

13. The pressure monitoring and warning device as recited in claim 12, wherein said warning device includes at least one LED light.

14. The pressure monitoring and warning device as recited in claim 13, and further including a DC power source connected to said switch for supplying power to said warning device.

15. The pressure monitoring and warning device as recited in claim 14, wherein said mount includes a base plate, said base plate configured to be mounted adjacent to an axle of the tow trailer.

16. The pressure monitoring and warning device as recited in claim 15, and further including a clamp, said clamp configured to releasably secure said base plate to said axle.

17. The device as recited in claim 16, wherein at least a portion of said warning device is disposed within a vehicle that is connectable connected to the tow trailer.

* * * * *